US012569638B2

(12) United States Patent
Jhuo et al.

(10) Patent No.: US 12,569,638 B2
(45) Date of Patent: Mar. 10, 2026

(54) VENTILATOR MASK AND JOINT THEREOF

(71) Applicant: BUDDHIST TZU CHI MEDICAL FOUNDATION, Xincheng Township Hualien County (TW)

(72) Inventors: Yi-Fong Jhuo, Hualien County (TW); Mei-Chin Hung, Hualien County (TW); Hsing-Long Lin, Hualien County (TW); Zu-Chun Lin, Hualien County (TW); Chia-Jung Chen, Hualien County (TW)

(73) Assignee: BUDDHIST TZU CHI MEDICAL FOUNDATION, Xincheng Township (TW)

( * ) Notice: Subject to any disclaimer, the term of this patent is extended or adjusted under 35 U.S.C. 154(b) by 681 days.

(21) Appl. No.: 17/977,434

(22) Filed: Oct. 31, 2022

(65) Prior Publication Data

US 2023/0144588 A1 May 11, 2023

(30) Foreign Application Priority Data

Nov. 5, 2021 (TW) ................................. 110141418

(51) Int. Cl.
*A61M 16/08* (2006.01)
*A61M 16/06* (2006.01)
*A61M 16/20* (2006.01)

(52) U.S. Cl.
CPC ........ *A61M 16/0833* (2014.02); *A61M 16/06* (2013.01); *A61M 16/208* (2013.01)

(58) Field of Classification Search
None
See application file for complete search history.

(56) References Cited

U.S. PATENT DOCUMENTS 9,604,027 B2 * 3/2017 Graham ............ A61M 16/0816
11,179,531 B2 * 11/2021 Brown .............. A61M 16/0493

* cited by examiner

*Primary Examiner* — Reginald S Tillman, Jr.
(74) *Attorney, Agent, or Firm* — Rosenberg, Klein & Lee

(57) ABSTRACT

A ventilator mask and a joint thereof are provided. The ventilator mask includes a ventilator mask body and the joint. The joint includes a joint body, an upper cover, and a perforated cover. The joint body includes a first end portion, a second end portion, and a third end portion. The first end portion is configured to be movably connected to the ventilator mask body. The third end portion is configured to communicate with an oxygen source. An opening is disposed between the first and second end portions. The upper cover is pivotally connected to the joint body for closing or opening the opening. The perforated cover is disposed on the second end portion. The perforated cover has a through hole for insertion of a tube. The ventilator mask can be airtightly fitted to the patient's face. There is no need to remove the ventilator mask for performing sputum suction.

18 Claims, 16 Drawing Sheets

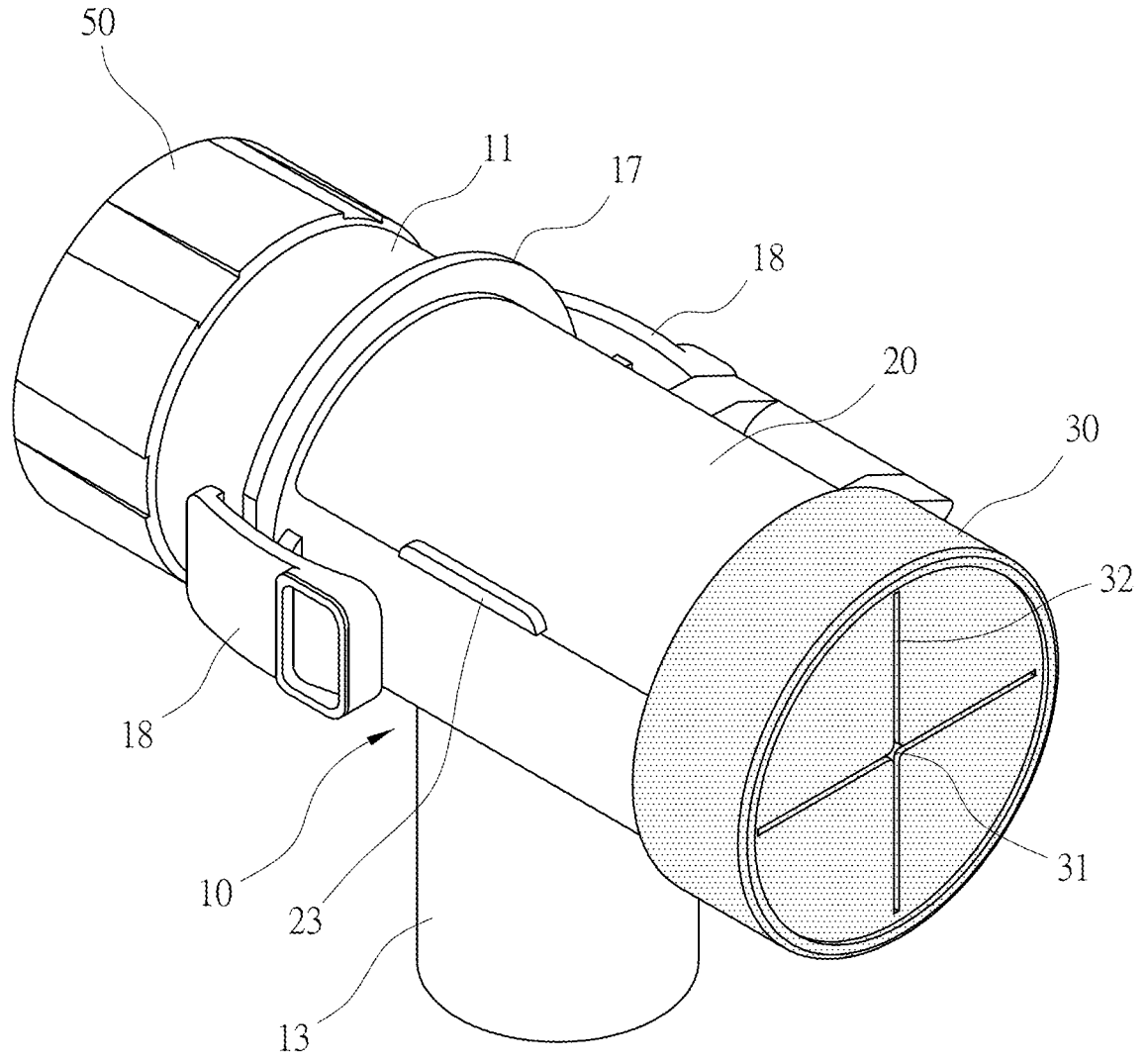
F I G . 1

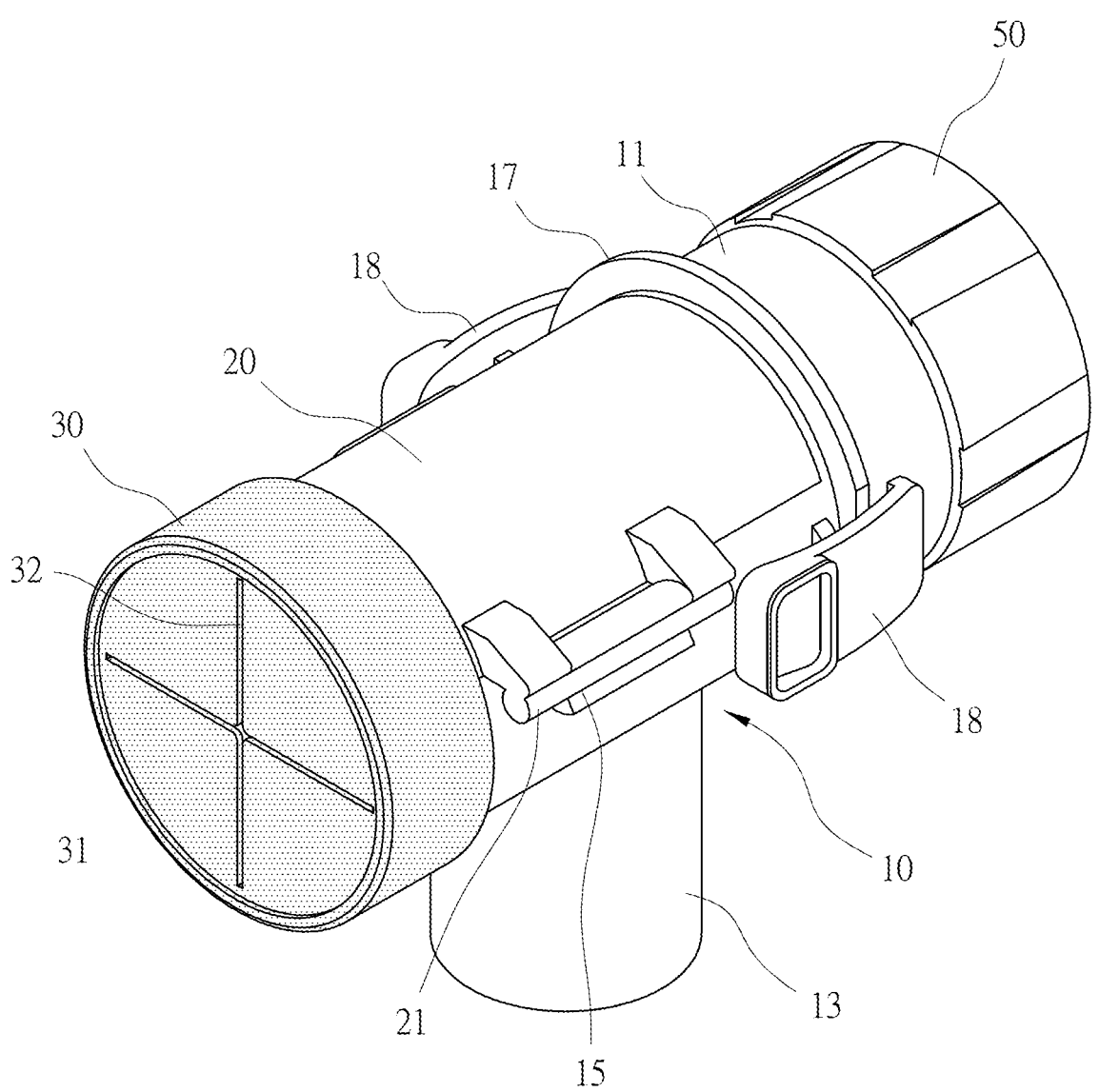
F I G . 2

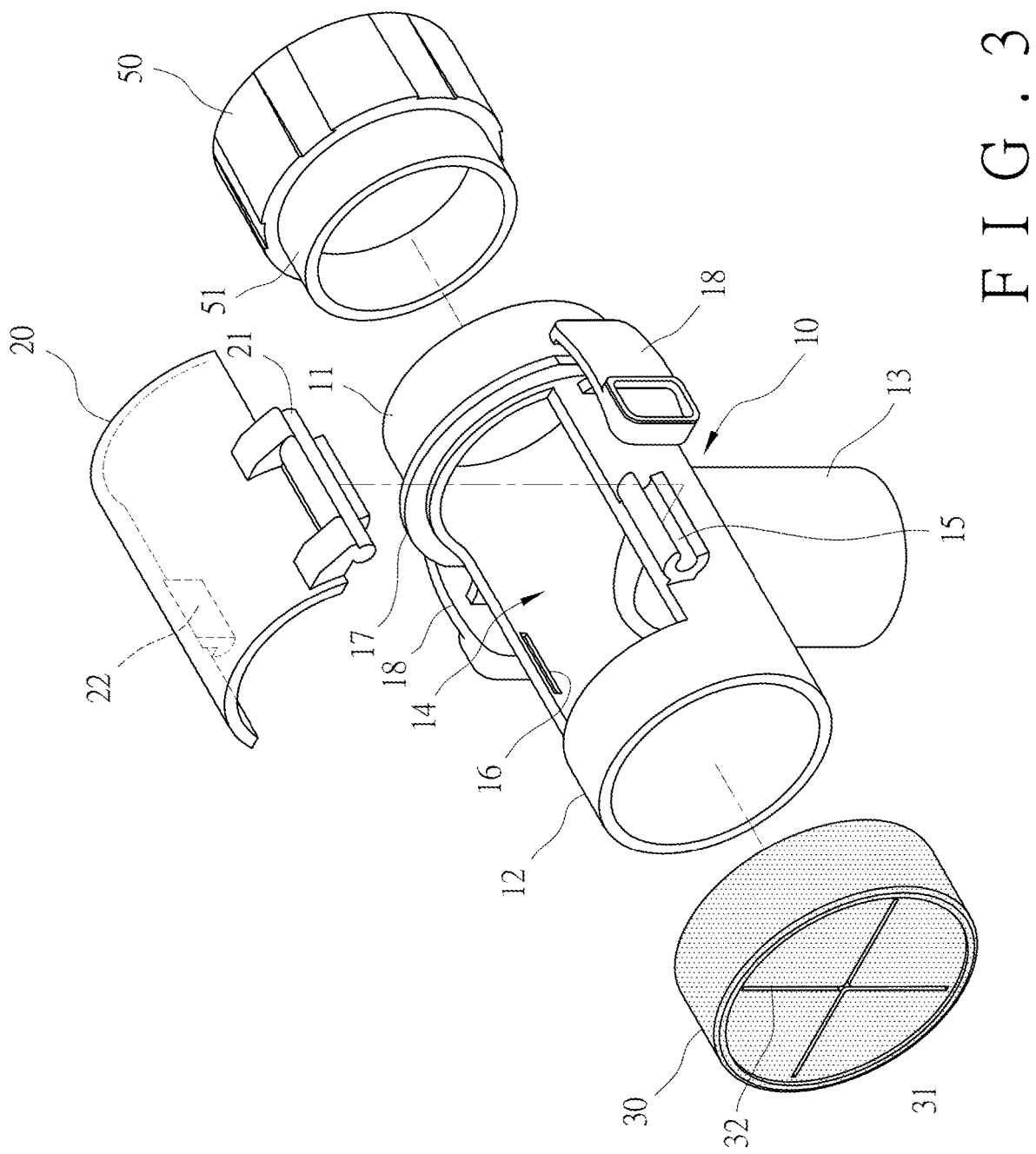
F I G . 3

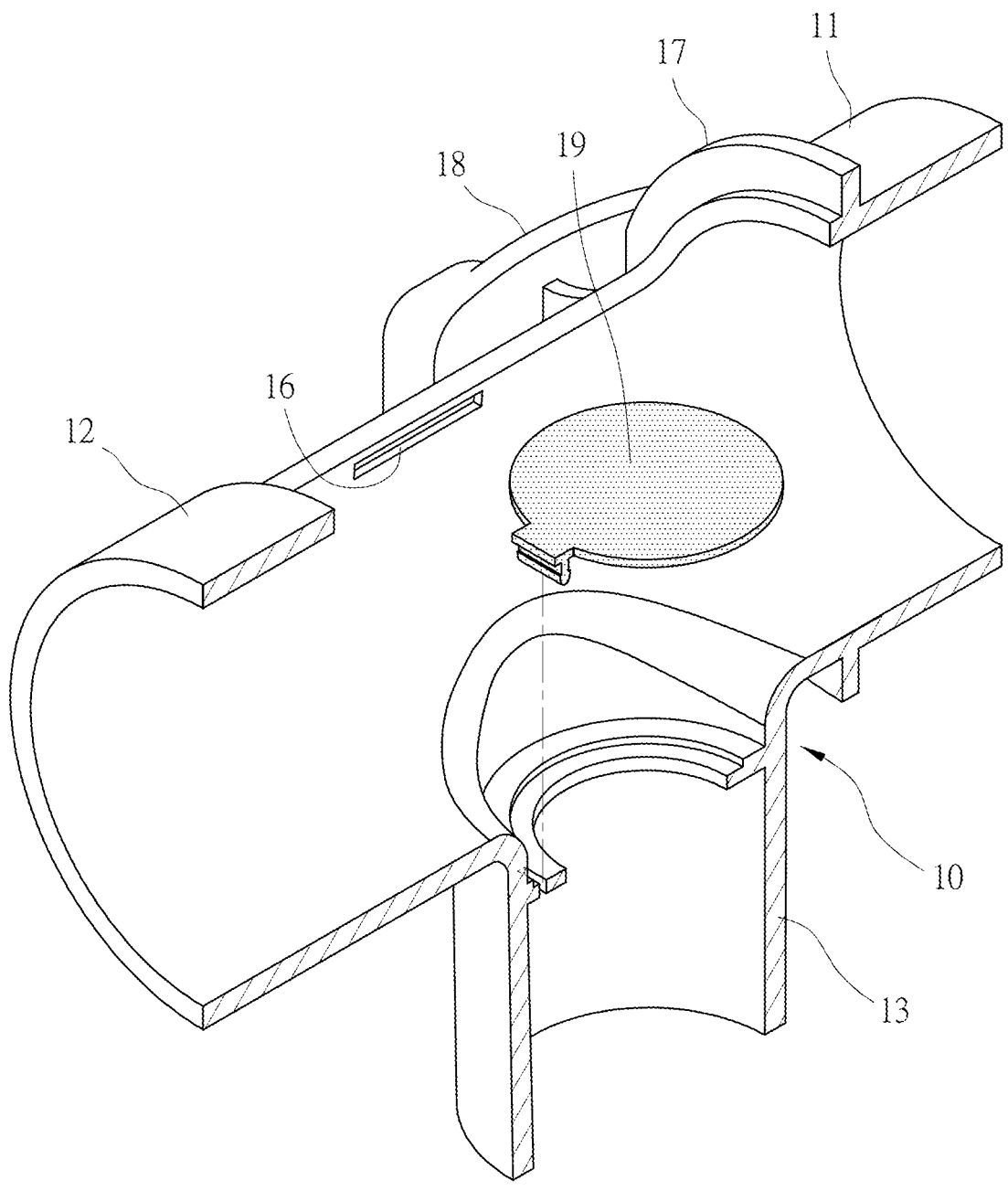
F I G . 4

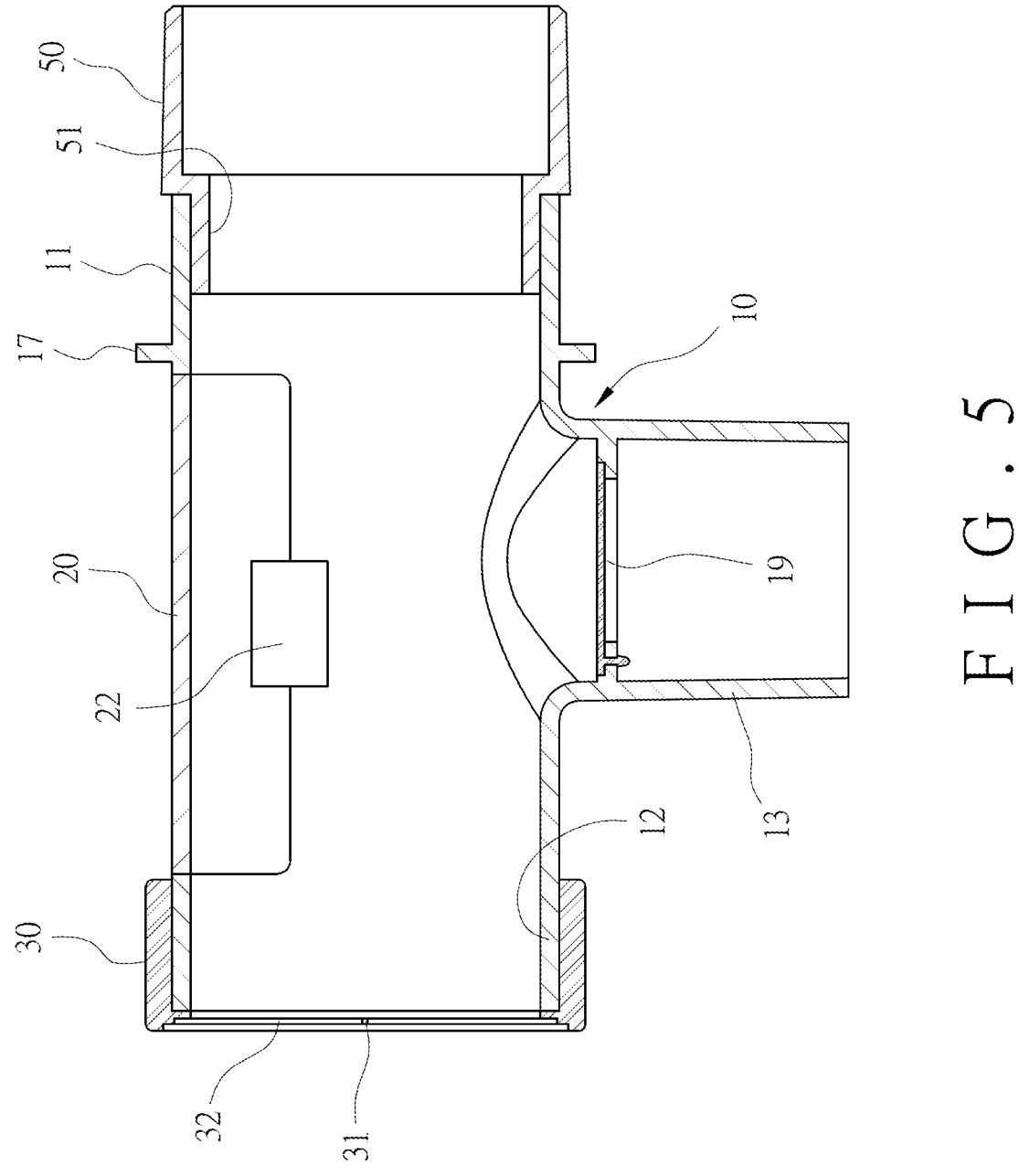
F I G . 5

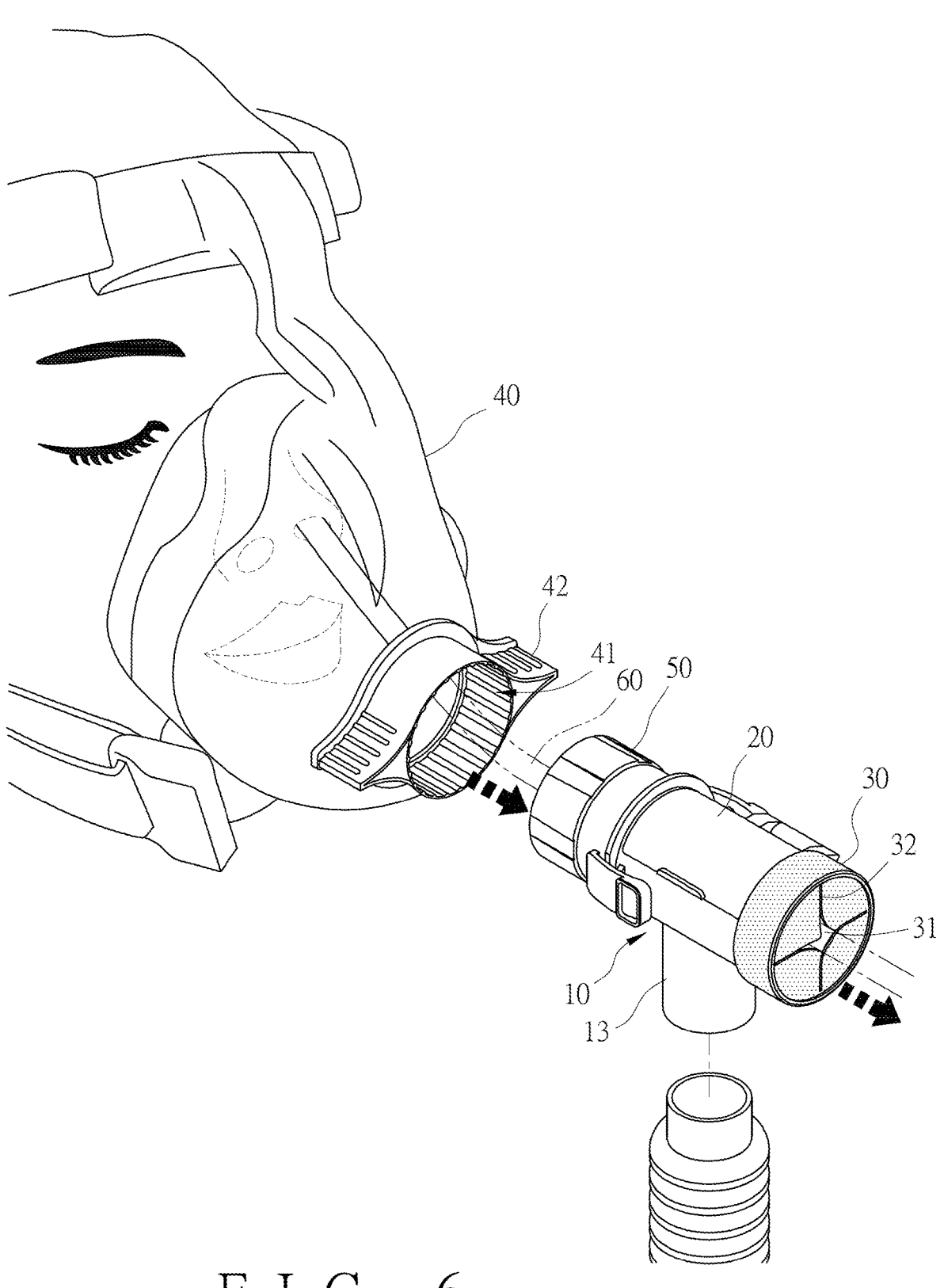
F I G . 6

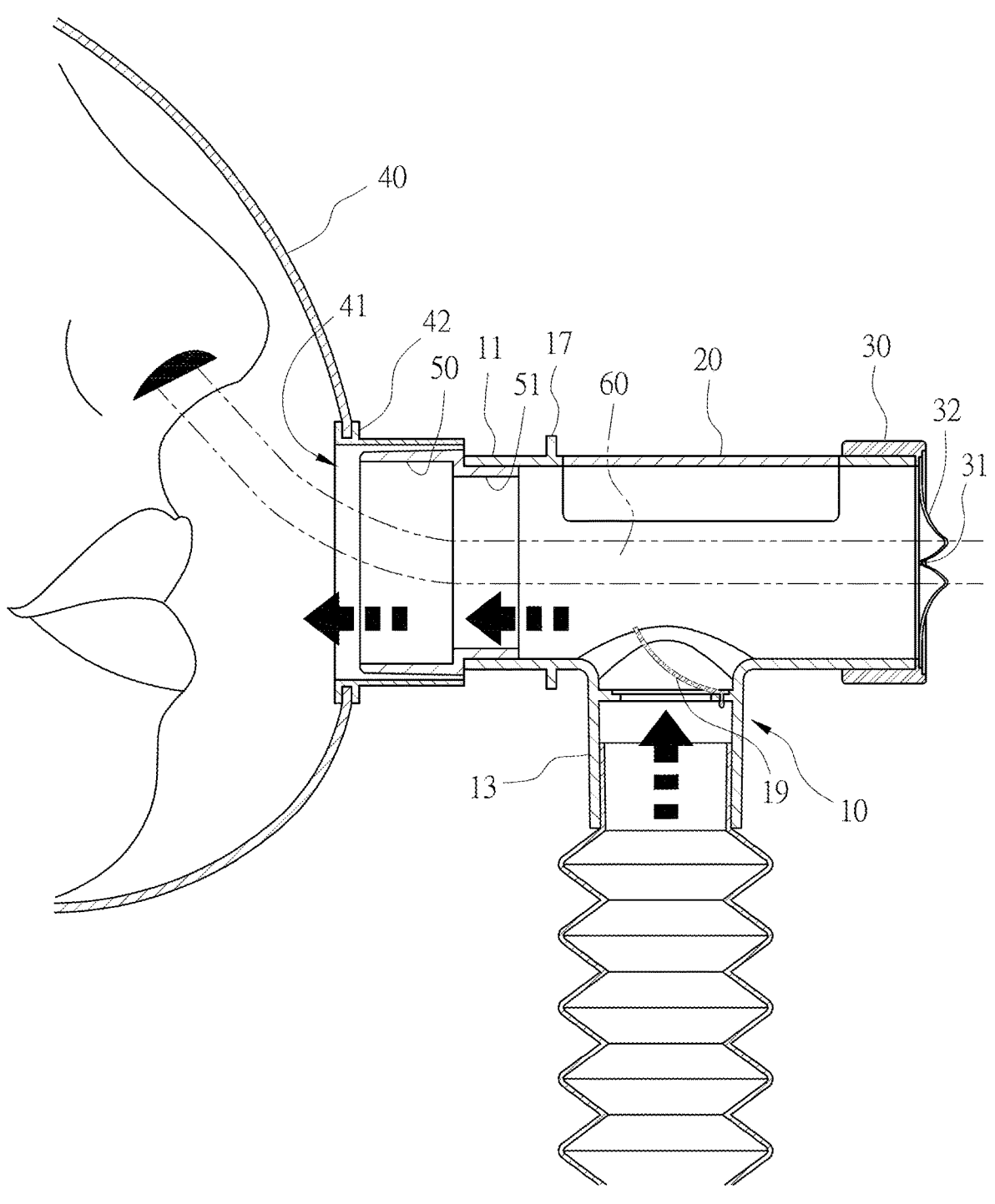
F I G . 7

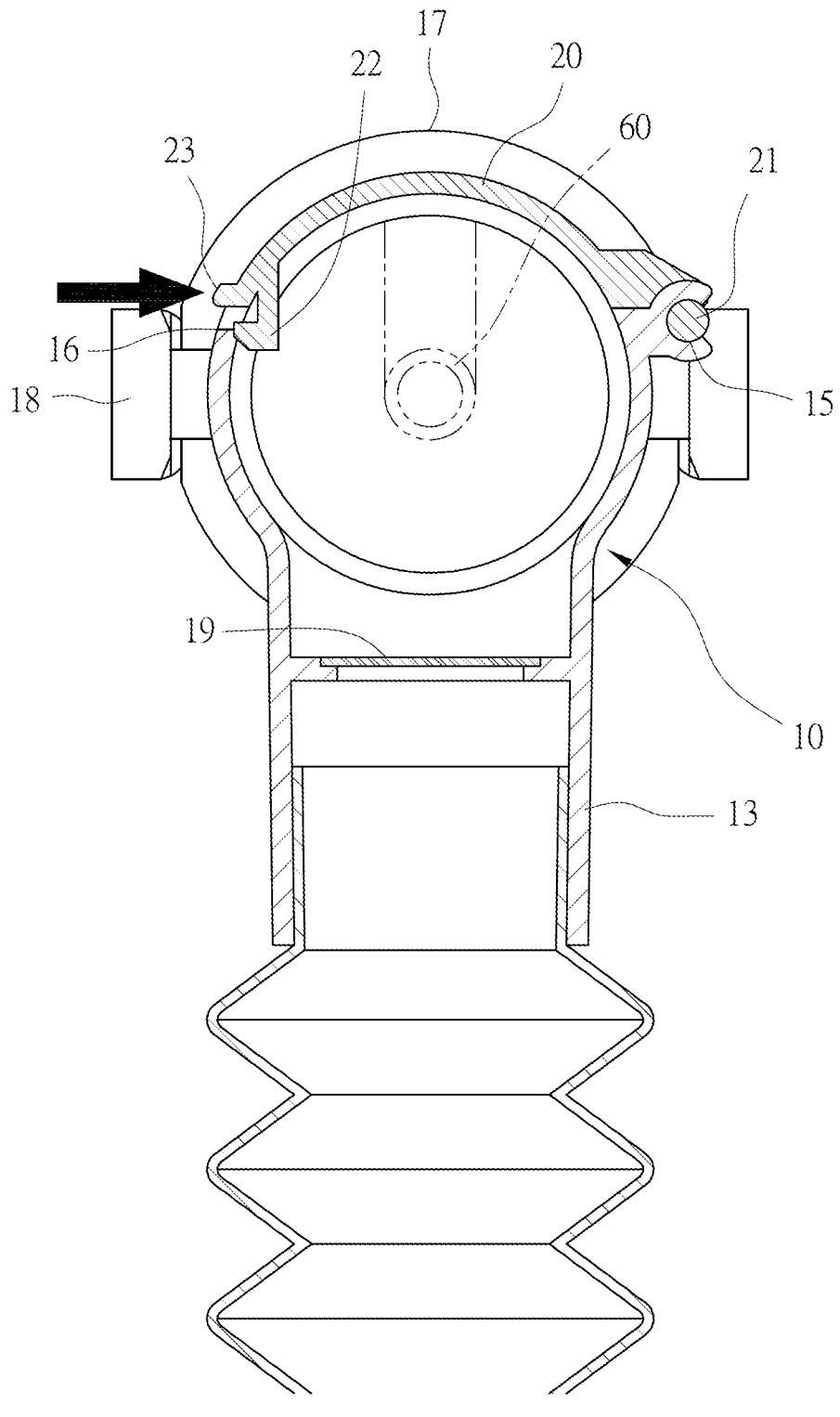
F I G . 8

F I G . 9

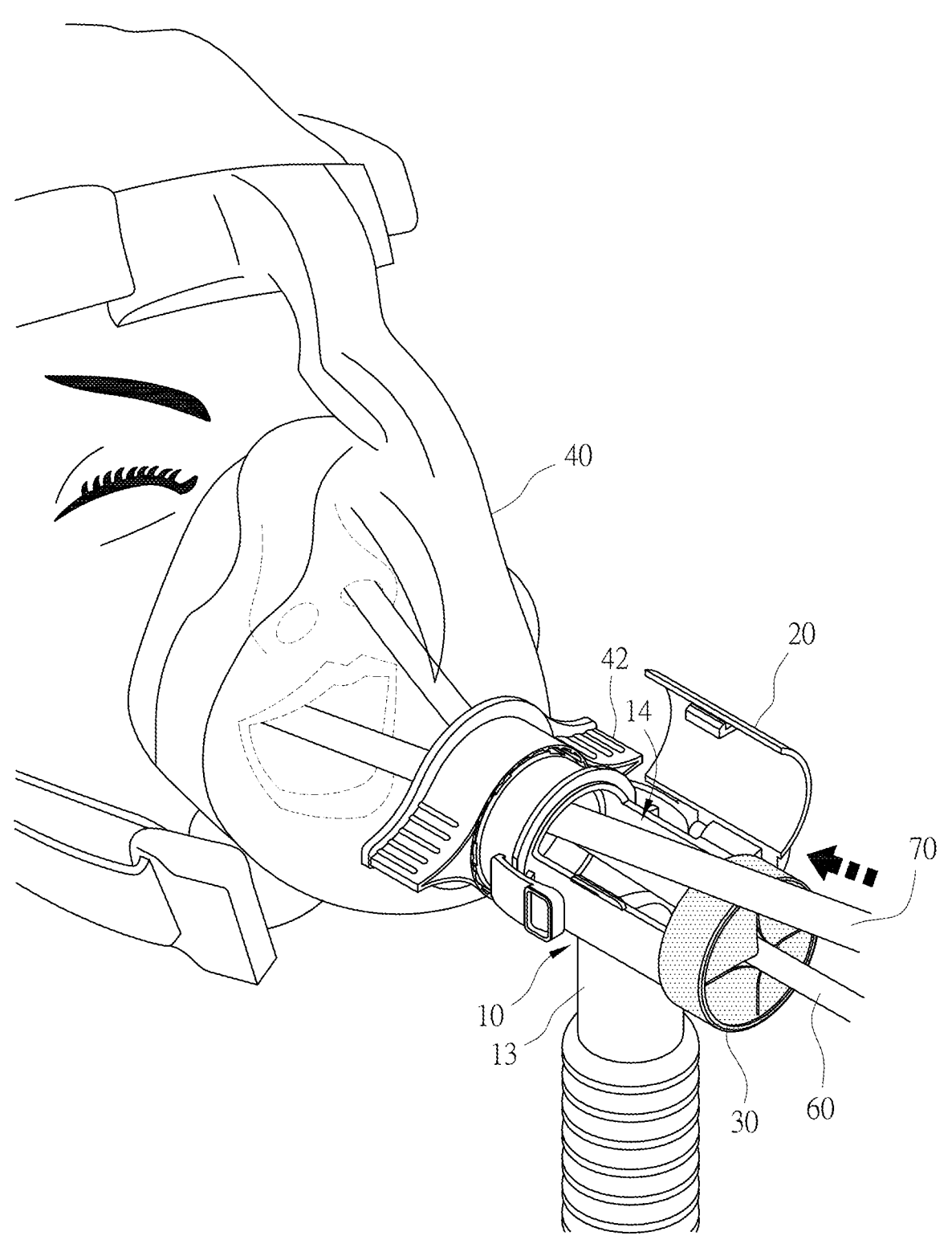
F I G . 10

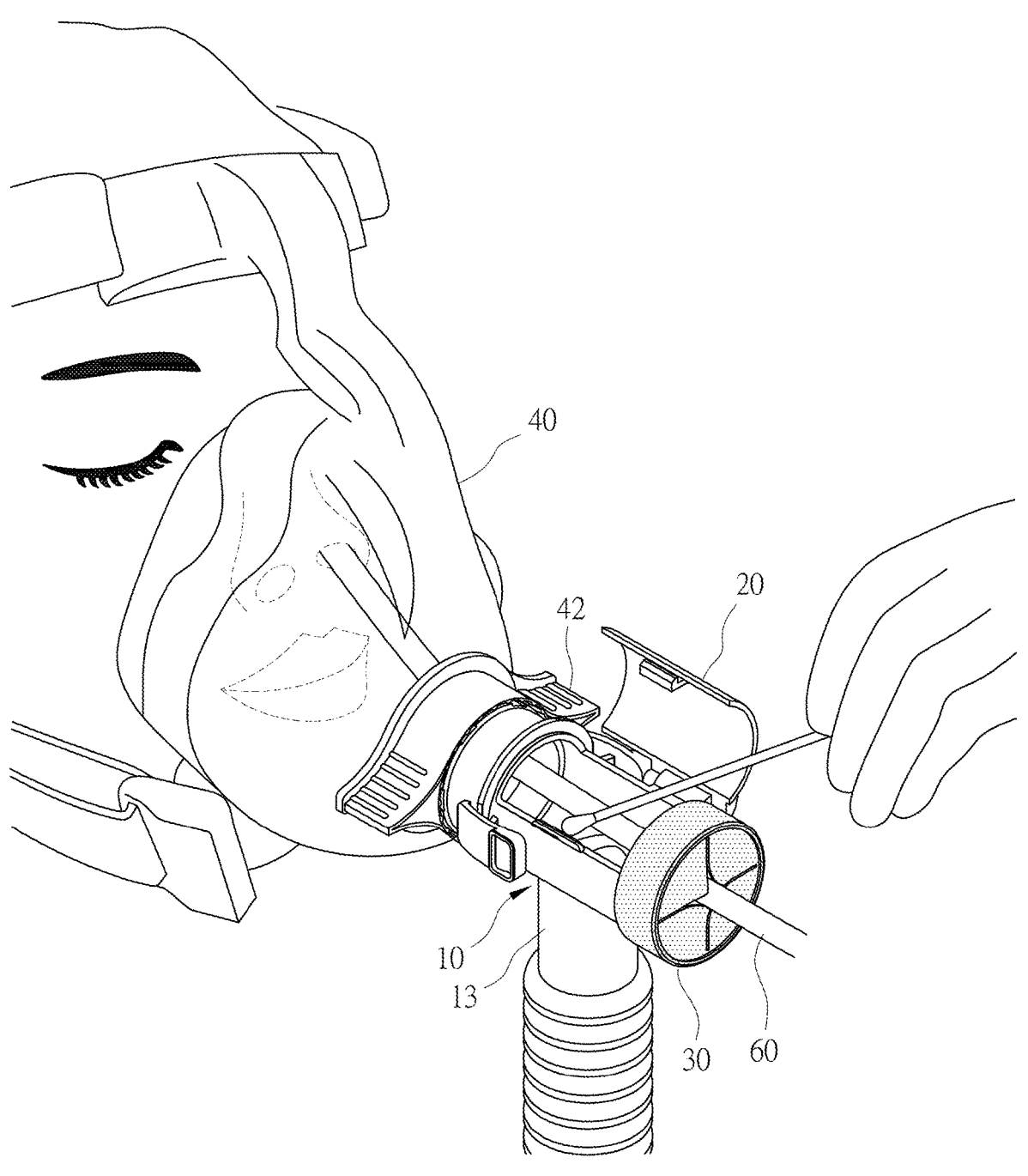
F I G . 11

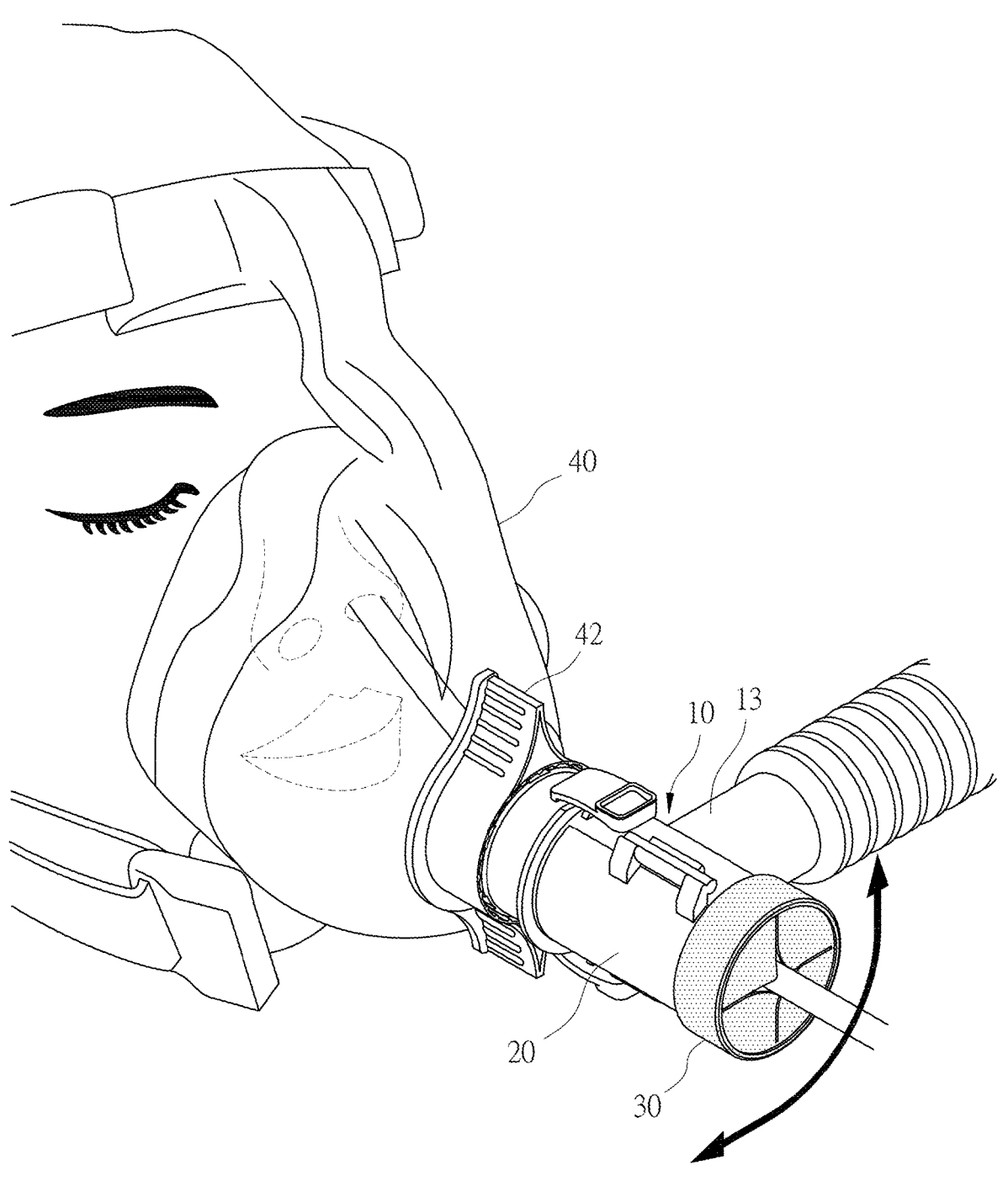
F I G . 12

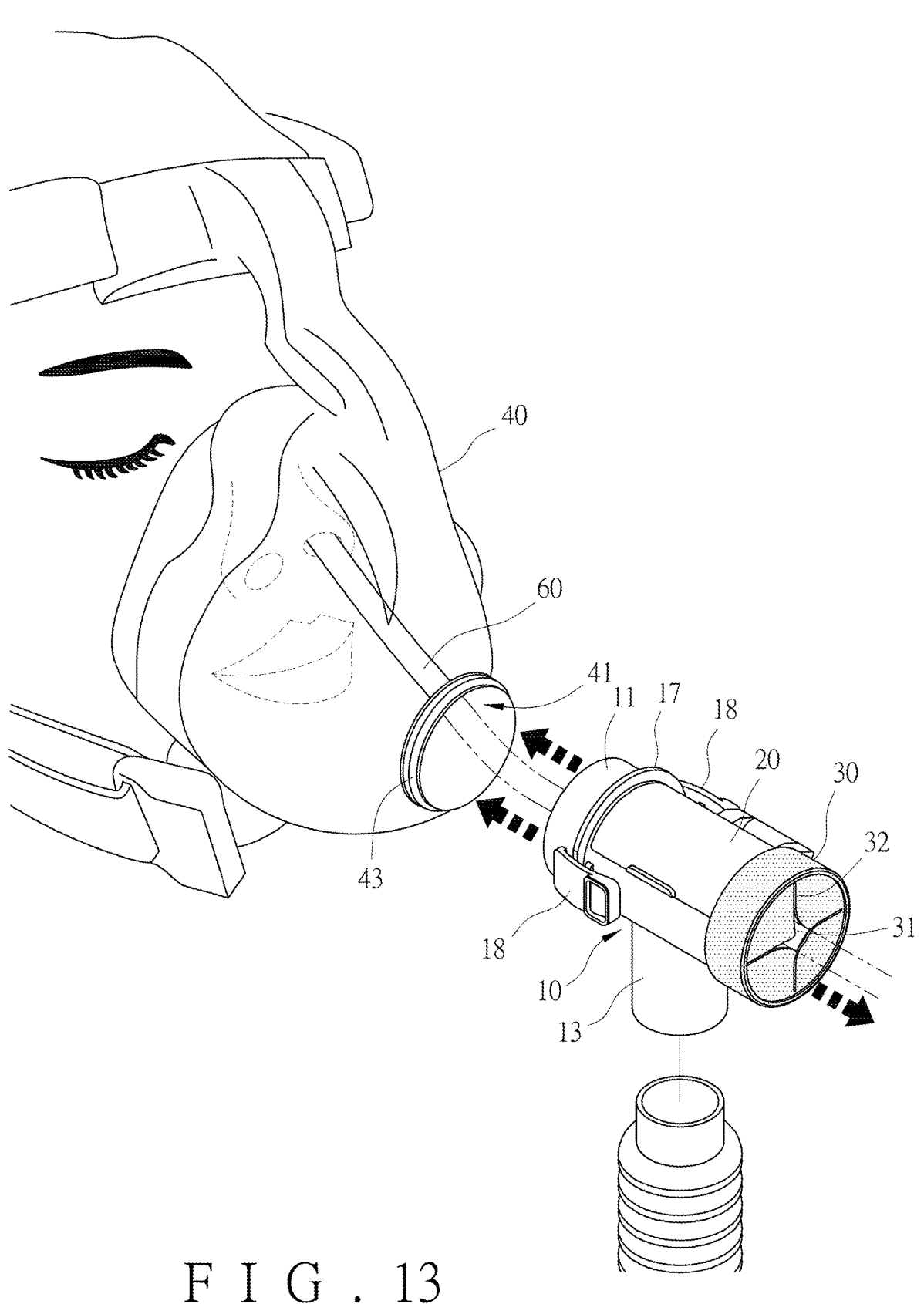
F I G . 13

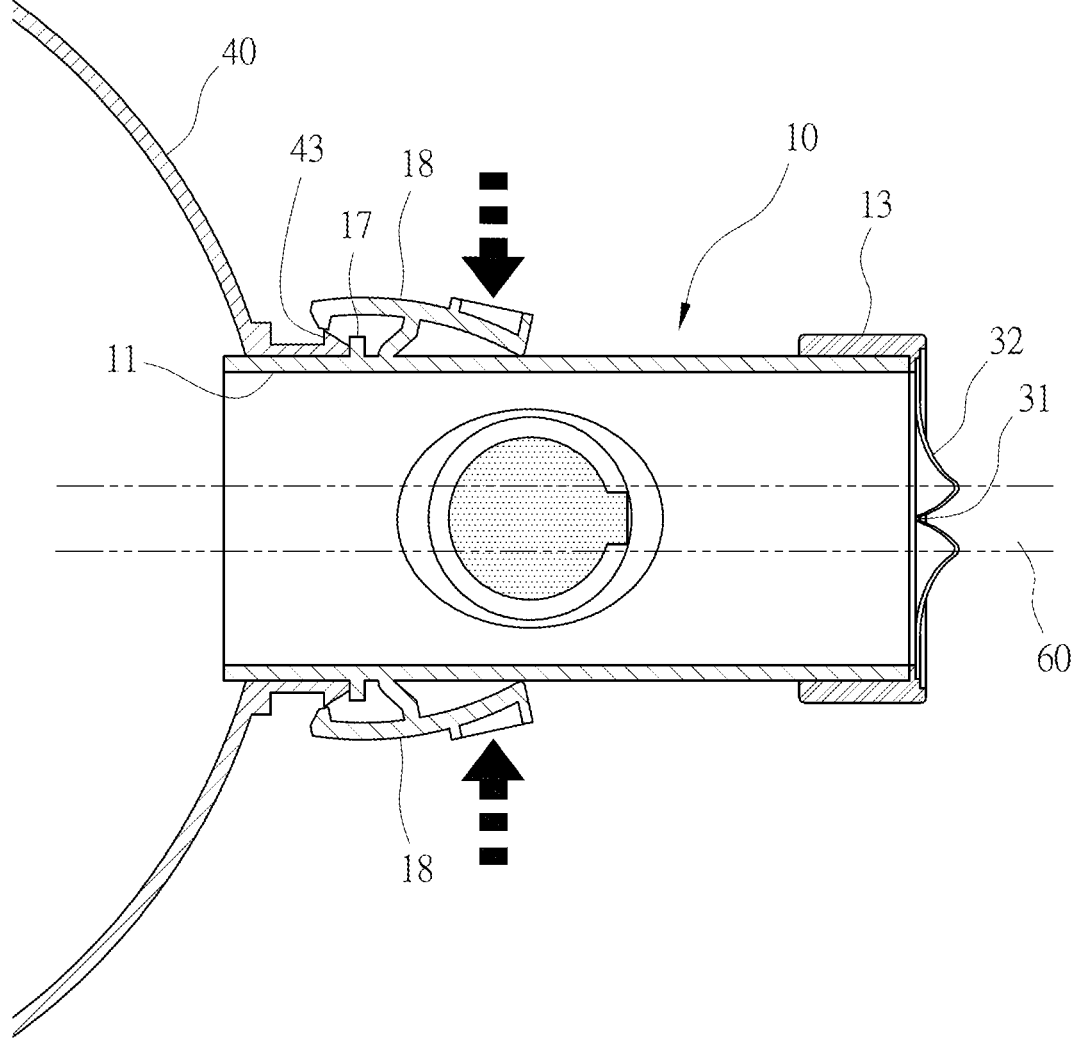
F I G . 14

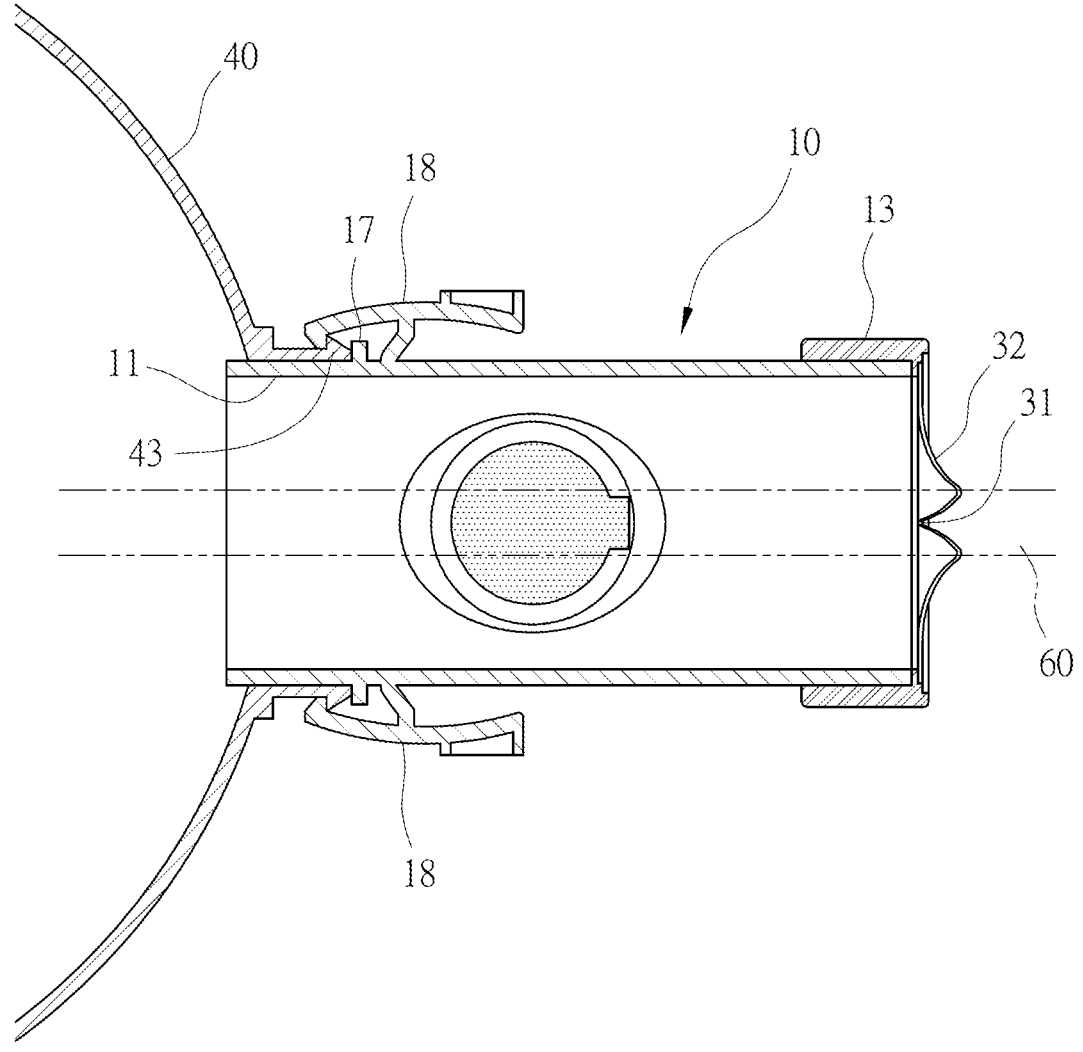
F I G . 15

F I G . 16

VENTILATOR MASK AND JOINT THEREOF

FIELD OF THE INVENTION

The present invention relates to a ventilator mask and a joint thereof, and more particularly to a ventilator mask using a joint to connect a naso-gastric tube and a sputum suction tube. The ventilator mask can be airtightly fitted to the patient's face. There is no need to remove the ventilator mask for performing sputum suction.

BACKGROUND OF THE INVENTION

Patients with respiratory failure use bilevel positive airway pressure (BiPAP) because they are unable to breathe on their own to bring sufficient oxygen to their whole body.

BiPAP is a type of noninvasive positive pressure ventilator. It is a pressure-support device driven by air flow and triggered by time cycle. It pushes air into the lungs and helps the lungs open up, allowing more oxygen into the lungs. When a patient is unable to breathe autonomously, or is able to breathe autonomously but unable to achieve required ventilation, BiPAP can provide air flow exceeding or equivalent to the maximum volume of air inhaled by the patient, meeting the patient's ventilation need.

BiPAP is used in postoperative ventilation, respiratory muscle failure, hypoxeia, post-extubation, intubation refusal, spinal injury, end-stage cancer patients, patients with upper respiratory tract obstruction, etc. A flexible tube is connected to either a full-face mask or a nasal mask on the patient's face. The BiPAP mask is a critical consumable because the machine's air supply and air delivery to the patient depend on it. Inappropriate material or design may cause uneven sealing and leakage, or cause pressure-induced skin injuries.

In clinical practice, patients using BiPAP usually also use naso-gastric tube or oral-gastric tube for the purpose of enteral feeding, medication administration or drainage. However, none of the BiPAP masks used in current clinical practice is designed for the placement of naso-gastric tube or oral-gastric tube, which is usually inserted into the mask from under its edges, causing an imperfect fit. If the mask is worn too loosely, it can cause leakage; if worn too tightly, it can cause pressure-induced injury, leading to pain or wound infection.

Furthermore, clinically, both internal medicine and surgical wards can encounter patients who are too weak or unable to voluntarily cough out secretions. In such situations, suctioning will be used to help them evacuate the secretions but the process may affect patients' oxygenation and improper operation may cause upper respiratory tract injury, infection and hypoxemia. Patients using BiPAP have to remove their mask completely for suctioning, which may reduce oxygen supply and increase the risk of hypoxemia.

Literature Review and Theoretical Foundation

1. Indications:

BiPAP is a type of noninvasive positive pressure ventilation (NIPPV). Most patients using NIPPV have chronic obstructive pulmonary disease, are end-stage cancer patients who refuse intubation, and/or have cardiopulmonary-related complications involving congestive heart failure and pulmonary edema caused by hypercapnia and hyponatremia.

By delivering positive pressure into the chest, noninvasive positive pressure ventilator may be used in treating moderate to severe acute respiratory failure. It is most effective in treating potential cardiogenic pulmonary edema because the positive end-expiratory pressure setting of the ventilator can prevent collapse of pulmonary air sacs, help to redistribute fluid with the air sacs, improve lung compliance and reduce respiratory pressure. It also improves breathing difficulty and oxygenation in patients with pulmonary edema. Noninvasive positive pressure ventilator is additionally effective in treating chronic obstructive pulmonary disease as positive end-expiratory pressure increases remaining capacity in the lungs. Besides increasing oxygenation, it also opens the airways and decreases the work of breathing.

2. Types of Ventilators and their Objectives:

The difference between noninvasive positive pressure ventilator and traditional positive pressure ventilator is the replacement of artificial airway with a full-face mask or nasal mask. There are generally two types of noninvasive positive pressure ventilator:

1. Continuous positive airway pressure (CPAP): The ventilator will maintain the same pressure whether during inspiration or expiration. It continuously delivers air into the airway and lungs, maintaining a certain level of pressure and allowing the lungs to expand, and expanding the body's ability to absorb oxygen.

2. Bilevel positive airway pressure (BiPAP): The ventilator delivers greater pressure during the patient's inspiration and smaller pressure during expiration. Besides increasing oxygen absorption, it also facilitates removal of carbon dioxide from the body.

Objectives of using noninvasive positive pressure ventilator:

1. Arterial blood gas analysis: Noninvasive positive pressure ventilator can improve PaO2 in patients with hypoxemic respiratory failure, and improve PaCO2 and PH in patients with both chronic obstructive pulmonary disease and hypercapnia respiratory failure.

2. Decreasing work of breathing: It reduces respiratory muscle activity, allowing respiratory muscles to rest so as to improve fatigue.

3. Comorbidity:

Common medical conditions that are simultaneously present when using the ventilator include: Gastric distension, mask leakage, oral dryness, conjunctiva irritation, nasal congestion and facial pressure ulcer. A study of patients in intensive care found that the incidence of pressure ulcer is 28.4%. Most injuries occur in the bony prominences, such as the coccyx, ischium and heel. It is noteworthy that the use of medical equipment, such as endotracheal tube, nasogastric tube, nasal cannula, plaster cast and NIPPV, may also cause pressure-induced injury. In cases where patients have a nasogastric tube temporarily in place to replenish nutrition and are being monitored for gastric distension, a mask that is worn too loose will cause leakage while one that is worn too tight will cause pressure-induced injury, resulting in such patients' pain and/or wound infection.

SUMMARY OF THE INVENTION

The primary object of the present invention is to provide a ventilator mask and a joint thereof. The ventilator mask can be airtightly fitted to the patient's face, and the patient's face won't be injured by the naso-gastric tube. There is no need to remove the ventilator mask for performing sputum suction.

In order to achieve the above object, the present invention provides a ventilator mask and a joint thereof. The ventilator mask comprises a ventilator mask body and the joint connected to the ventilator mask body. The joint comprises a joint body, an upper cover, and a perforated cover. The joint body has a T shape. The joint body includes a first end portion, a second end portion and a third end portion that communicate with each other. The first end portion is configured to be movably connected to the ventilator mask body. The third end portion is configured to communicate with an oxygen source. An opening is disposed between the first end portion and the second end portion. The upper cover is pivotally connected to the joint body for closing or opening the opening. The perforated cover is disposed on the second end portion. The perforated cover has a through hole for insertion of a tube.

Further, the joint body has a pivot groove close to the opening. One side of the upper cover has a pivot shaft corresponding to the pivot groove. The pivot shaft is inserted into the pivot groove so that the upper cover is pivotally connected to the joint body.

Further, an inner wall of the joint body has a locking groove close to the opening. A lower surface of the upper cover has a locking member corresponding to the locking groove. When the upper cover closes the opening, the locking member is engaged with the locking groove to secure the upper cover.

Further, an upper surface of the upper cover has a pull portion for the upper cover to be opened with a user's fingers.

Further, the first end portion is connected to a connector. The connector is movably connected to the ventilator mask body. The connector has a connecting portion. The connecting portion is detachably connected to the first end portion. Further, the ventilator mask body has a perforation and a coupling portion at the perforation. The connector is configured to fit the coupling portion. The connector is detachably connected to the coupling portion.

Further, the first end portion has a flange and a plurality of elastic hooks close to the flange. The elastic hooks are made of an elastic material and are elastically deformable. The elastic hooks each have a hook portion spanning the flange, so that the flange and the elastic hooks constitute a snap-fit structure for the joint body to be movably connected to the ventilator mask body. Further, the ventilator mask body has a perforation and an engaging portion at the perforation. When another end of each elastic hook is pressed, the hook portion of each elastic hook is lifted upward, and the first end portion is directly inserted into the perforation of the ventilator mask body until the first end portion is stopped by the flange. At this time, the another end of each elastic hook is released, and the hook portion of each elastic hook is elastically returned downward to snap the engaging portion against the flange so that the first end portion is movably connected to the engaging portion.

Further, the perforated cover is made of an elastic material and has a plurality of slits. The slits communicate with the through hole. When the tube has a diameter greater than that of the through hole, the vicinity of the through hole can be elastically deformed through the slits for the tube to pass through the through hole.

According to the above technical features, the following effects can be achieved:

1. For a patient using a naso-gastric tube, the naso-gastric tube extends out of the ventilator mask body from the perforation of the ventilator mask body, and then the naso-gastric tube is inserted through the joint body and the perforated cover, such that the ventilator mask body can be airtightly fitted to the patient's face, so as to prevent the patient's face from being injured by the naso-gastric tube.

2. When it is necessary to suction sputum for the patient, the upper cover is opened, and the sputum suction tube can be directly inserted through the opening of the joint body and the perforation of the ventilator mask body to enter the nasal cavity or oral cavity of the patient for performing sputum suction. There is no need to remove the ventilator mask body 40 for performing sputum suction.

BRIEF DESCRIPTION OF THE DRAWINGS

FIG. 1 is a perspective view of the present invention;

FIG. 2 is another perspective view of the present invention;

FIG. 3 is an exploded view of the present invention;

FIG. 4 is a cross-sectional view of the present invention, showing that the valve plate is disposed inside the joint body;

FIG. 5 is a cross-sectional view of the present invention;

FIGS. 6-12 are schematic views of the present invention applied to a PHILIPS mask when in use; and FIGS. 13-16 are schematic views of the present invention applied to a ResMed mask when in use.

DETAILED DESCRIPTION OF THE PREFERRED EMBODIMENTS

Embodiments of the present invention will now be described, by way of example only, with reference to the accompanying drawings.

Please refer to FIG. 1, FIG. 2, FIG. 3, FIG. 4, FIG. 5, and FIG. 6. A ventilator mask according to an embodiment of the present invention comprises a joint coupled to a ventilator mask body 40. The joint includes a joint body 10, an upper cover 20, and a perforated cover 30.

The joint body 10 is T-shaped. The joint body 10 includes a first end portion 11, a second end portion 12 and a third end portion 13 that communicate with each other. The first end portion 11 is movably connected to the ventilator mask body 40. The third end portion 13 is configured to communicate with an oxygen source. An opening 14 is disposed between the first end portion 11 and the second end portion 12.

The upper cover 20 is pivotally connected to the joint body 10 for closing or opening the opening 14.

The perforated cover 30 is disposed on the second end portion 12. The perforated cover 30 has a through hole 31 for insertion of a tube.

In a structural embodiment, the joint body 10 has a pivot groove 15 close to the opening 14. One side of the upper cover 20 has a pivot shaft 21 corresponding to the pivot groove 15. The pivot shaft 21 is inserted into the pivot groove 15 so that the upper cover 20 is pivotally connected to the joint body 10.

In a structural embodiment, the inner wall of the joint body 10 has a locking groove 16 close to the opening 14. The lower surface of the upper cover 20 has a locking member 22 corresponding to the locking groove 16. When the upper cover 20 closes the opening 14, the locking member 22 is engaged with the locking groove 16 to secure the upper cover 20.

The upper surface of the upper cover 20 has a pull portion 23, which can be pulled by fingers to open the upper cover 20 easily and effortlessly.

In a structural embodiment, the first end portion 11 is connected to a connector 50. The connector 50 is movably connected to the ventilator mask body 40. The connector 50 has a connecting portion 51. The connecting portion 51 is detachably connected to the first end portion 11, so as to facilitate assembly or disassembly of the connector 50 at the first end portion 11.

In a structural embodiment, the first end portion 11 has a flange 17 and a plurality of elastic hooks 18 close to the flange 17. The elastic hooks 18 are made of an elastic material and can be elastically deformed. The elastic hooks 18 each have a hook portion spanning the flange 17. The flange 17 and the elastic hooks 18 form a snap-fit structure for the joint body 10 to be movably connected to the ventilator mask body 40.

In a structural embodiment, a valve plate 19 is provided at the junction of the first end portion 11, the second end portion 12 and the third end portion 13. One end of the valve plate 19 is fixed. The valve plate 19 is made of an elastic material and can be elastically deformed to close the junction of the first end portion 11, the second end portion 12 and the third end portion 13. The oxygen supplied from the oxygen source can push the valve plate 19 open in only one direction to enter the first end portion 11 and the second end portion 12. The valve plate 19 has a non-return effect.

In a structural embodiment, the perforated cover 30 is made of an elastic material and has a plurality of slits 32. The slits 32 communicate with the through hole 31. When a tube with a diameter greater than the through hole 31, the vicinity of the through hole 31 can be elastically deformed through the slits 32 for the tube to pass through the through hole 31.

The foregoing description relates to the components and assembly of the present invention. Next, the use characteristics and effects of the present invention are described below.

Please refer to FIG. 6 and FIG. 7. In this embodiment, the ventilator mask body 40 is selected from PHILIPS masks. For a patient using a naso-gastric tube, the naso-gastric tube 60 extends out of the ventilator mask body 40 from a perforation 41 of the ventilator mask body 40, and then the naso-gastric tube 60 is inserted through the joint body 10 and the through hole 31 of the perforated cover 30.

The ventilator mask body 40 has a coupling portion 42 at the perforation 41. The connector 50 is configured to fit the coupling portion 42. The connector 50 is insertedly, detachably connected to the coupling portion 42, so that the joint body 10 is connected to the ventilator mask body 40.

The third end portion 13 is connected to an elastic breathing tube to communicate with the oxygen source, such as a BiPAP ventilator, so that the oxygen from the oxygen source can be supplied to the patient through the joint body 10 and the ventilator mask body 40.

Accordingly, the ventilator mask body 40 can be airtightly fitted to the patient's face, so as to prevent the patient's face from being injured by the naso-gastric tube 60.

Please refer to FIG. 8, FIG. 9, and FIG. 10. When it is necessary to suction sputum for the patient, the upper cover 20 is opened, and the sputum suction tube 70 can be directly inserted through the opening 14 of the joint body 10 and the perforation 41 of the ventilator mask body 40 to enter the nasal cavity or oral cavity of the patient for performing sputum suction. There is no need to remove the ventilator mask body 40 for performing sputum suction.

Please refer to FIG. 11. After performing sputum suction, the upper cover 20 is opened, and a cotton swab is used to clean the sputum/dirt remaining in the joint body 10, so as to provide a hygienic effect.

Please refer to FIG. 12. The joint body 10 of the present invention and the coupling portion 42 of the ventilator mask body 40 can be rotated together for adjusting the air supply angle of the joint body 10.

Please refer to FIG. 13, FIG. 14, and FIG. 15. In this embodiment, the ventilator mask body 40 is selected from ResMed masks. First, the connector 50 is removed from the joint body 10. Similarly, the naso-gastric tube 60 extends out of the ventilator mask body 40 from the perforation 41 of the ventilator mask body 40, and then the naso-gastric tube 60 is inserted through the joint body 10 and the through hole 31 of the perforated cover 30.

The ventilator mask body 40 has an engaging portion 43 at the perforation 41. When the other end of the elastic hook 18 is pressed, the hook portion of the elastic hook 18 is lifted upward, and the first end portion 11 can be directly inserted into the perforation 41 of the ventilator mask body 40 until it is stopped by the flange 17. At this time, the other end of the elastic hook 18 is released, and the hook portion of the elastic hook 18 is elastically returned downward to snap the engaging portion 43 against the flange 17. The first end portion 11 is movably connected to the engaging portion 43, so that the joint body 10 can be connected to the ventilator mask body 40 easily.

Similarly, the third end portion 13 is connected to an elastic breathing tube to communicate with the oxygen source, such as a BiPAP ventilator, so that the oxygen from the oxygen source can be supplied to the patient through the joint body 10 and the ventilator mask body 40.

Accordingly, the ventilator mask body 40 can be airtightly fitted to the patient's face, so as to prevent the patient's face from being injured by the naso-gastric tube 60.

Please refer to FIG. 16. Because the elastic hook 18 and the engaging portion 43 are elastically buckled on the flange 17, the joint body 10 can rotate relative to the perforation 41 of the ventilator mask body 40 so that the air supply angle of the joint body 10 can be adjusted freely.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A joint for a ventilator mask, comprising:
a joint body, having a T shape, the joint body including a first end portion, a second end portion, and a third end portion that communicate with each other, the first end portion being configured to be movably connected to a ventilator mask body, the third end portion being configured to communicate with an oxygen source, an opening being disposed between the first end portion and the second end portion;
an upper cover, pivotally connected to the joint body for closing or opening the opening; and
a perforated cover, disposed on the second end portion, the perforated cover having a through hole configured for insertion of a first tube;
wherein the second end portion and the first end portion define ends of a first insertion path through the joint body configured for insertion of the first tube therethrough, and the opening and the first end portion define ends of a second insertion path through the joint body configured for insertion of a second tube therethrough alongside the first tube, and
wherein a valve plate is provided at a junction of the first end portion, the second end portion, and the third end portion, one end of the valve plate is fixed, the valve plate is made of an elastic material and is elastically deformable, the valve plate is configured to close the junction of the first end portion, the second end portion and the third end portion, and oxygen supplied from the oxygen source pushes the valve plate open in only one direction to enter the first end portion and the second end portion.

2. The joint as claimed in claim 1, wherein the joint body has a pivot groove close to the opening, one side of the upper cover has a pivot shaft corresponding to the pivot groove, and the pivot shaft is inserted into the pivot groove so that the upper cover is pivotally connected to the joint body.

3. The joint as claimed in claim 1, wherein an inner wall of the joint body has a locking groove close to the opening, a lower surface of the upper cover has a locking member corresponding to the locking groove, when the upper cover closes the opening, the locking member is engaged with the locking groove to secure the upper cover.

4. The joint as claimed in claim 1, wherein an upper surface of the upper cover has a pull portion for the upper cover to be opened with a user's fingers.

5. The joint as claimed in claim 1, wherein the first end portion is connected to a connector, the connector is movably connected to the ventilator mask body, the connector has a connecting portion, and the connecting portion is detachably connected to the first end portion.

6. The joint as claimed in claim 5, wherein the ventilator mask body has a perforation and a coupling portion at the perforation, the connector is configured to fit the coupling portion, and the connector is detachably connected to the coupling portion.

7. The joint as claimed in claim 1, wherein the first end portion has a flange and a plurality of elastic hooks close to the flange, the elastic hooks are made of an elastic material and are elastically deformable, and the elastic hooks each have a hook portion spanning the flange, so that the flange and the elastic hooks constitute a snap-fit structure for the joint body to be movably connected to the ventilator mask body.

8. The joint as claimed in claim 7, wherein the ventilator mask body has a perforation and an engaging portion at the perforation, when another end of each elastic hook is pressed, the hook portion of each elastic hook is lifted upward, and the first end portion is directly inserted into the perforation of the ventilator mask body until the first end portion is stopped by the flange, at this time, the another end of each elastic hook is released, and the hook portion of each elastic hook is elastically returned downward to snap the engaging portion against the flange so that the first end portion is movably connected to the engaging portion.

9. The joint as claimed in claim 1, wherein the perforated cover is made of an elastic material and has a plurality of slits, the slits communicate with the through hole, when the first tube has a diameter greater than that of the through hole, the vicinity of the through hole can be elastically deformed through the slits for the first tube to pass through the through hole.

10. A ventilator mask, comprising:
a ventilator mask body;
a joint, including:
a joint body, having a T shape, the joint body including a first end portion, a second end portion, and a third end portion that communicate with each other, the first end portion being configured to be movably connected to the ventilator mask body, the third end portion being configured to communicate with an oxygen source, an opening being disposed between the first end portion and the second end portion;
an upper cover, pivotally connected to the joint body for closing or opening the opening; and
a perforated cover, disposed on the second end portion, the perforated cover having a through hole configured for insertion of a first tube;
wherein the second end portion and the first end portion define ends of a first insertion path through the joint body configured for insertion of the first tube therethrough, and the opening and the first end portion define ends of a second insertion path through the joint body configured for insertion of a second tube therethrough alongside the first tube, and
wherein a valve plate is provided at a junction of the first end portion, the second end portion, and the third end portion, one end of the valve plate is fixed, the valve plate is made of an elastic material and is elastically deformable, the valve plate is configured to close the junction of the first end portion, the second end portion and the third end portion, and oxygen supplied from the oxygen source pushes the valve plate open in only one direction to enter the first end portion and the second end portion.

11. The ventilator mask as claimed in claim 10, wherein the joint body has a pivot groove close to the opening, one side of the upper cover has a pivot shaft corresponding to the pivot groove, and the pivot shaft is inserted into the pivot groove so that the upper cover is pivotally connected to the joint body.

12. The ventilator mask as claimed in claim 10, wherein an inner wall of the joint body has a locking groove close to the opening, a lower surface of the upper cover has a locking member corresponding to the locking groove, when the upper cover closes the opening, the locking member is engaged with the locking groove to secure the upper cover.

13. The ventilator mask as claimed in claim 10, wherein an upper surface of the upper cover has a pull portion for the upper cover to be opened with a user's fingers.

14. The ventilator mask as claimed in claim 10, wherein the first end portion is connected to a connector, the connector is movably connected to the ventilator mask body, the connector has a connecting portion, and the connecting portion is detachably connected to the first end portion.

15. The ventilator mask as claimed in claim 14, wherein the ventilator mask body has a perforation and a coupling portion at the perforation, the connector is configured to fit the coupling portion, and the connector is detachably connected to the coupling portion.

16. The ventilator mask as claimed in claim 10, wherein the first end portion has a flange and a plurality of elastic hooks close to the flange, the elastic hooks are made of an elastic material and are elastically deformable, and the elastic hooks each have a hook portion spanning the flange, so that the flange and the elastic hooks constitute a snap-fit structure for the joint body to be movably connected to the ventilator mask body.

17. The ventilator mask as claimed in claim 16, wherein the ventilator mask body has a perforation and an engaging portion at the perforation, when another end of each elastic hook is pressed, the hook portion of each elastic hook is lifted upward, and the first end portion is directly inserted into the perforation of the ventilator mask body until the first end portion is stopped by the flange, at this time, the another end of each elastic hook is released, and the hook portion of each elastic hook is elastically returned downward to snap the engaging portion against the flange so that the first end portion is movably connected to the engaging portion.

18. The ventilator mask as claimed in claim 10, wherein the perforated cover is made of an elastic material and has a plurality of slits, the slits communicate with the through hole, when the first tube has a diameter greater than that of the through hole, the vicinity of the through hole is elastically deformed through the slits for the first tube to pass through the through hole.

\* \* \* \* \*